(12) United States Patent
Dennerlein et al.

(10) Patent No.: US 9,271,691 B2
(45) Date of Patent: Mar. 1, 2016

(54) METHOD AND X-RAY DEVICE TO DETERMINE A THREE-DIMENSIONAL TARGET IMAGE DATA SET

(71) Applicants: Frank Dennerlein, Forchheim (DE); Mathias Hoernig, Erlangen (DE)

(72) Inventors: Frank Dennerlein, Forchheim (DE); Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 73 days.

(21) Appl. No.: 13/970,760

(22) Filed: Aug. 20, 2013

(65) Prior Publication Data

US 2014/0050295 A1  Feb. 20, 2014

(30) Foreign Application Priority Data

Aug. 20, 2012  (DE) .......................... 10 2012 214 735

(51) Int. Cl.
  *A61B 6/00*  (2006.01)
  *A61B 6/03*  (2006.01)
  *G06T 11/00*  (2006.01)

(52) U.S. Cl.
  CPC . *A61B 6/52* (2013.01); *A61B 6/032* (2013.01); *A61B 6/4441* (2013.01); *A61B 6/488* (2013.01); *A61B 6/5205* (2013.01); *G06T 11/005* (2013.01)

(58) Field of Classification Search
  CPC ...... B25J 9/1666; B25J 9/1682; A61B 6/032; A61B 6/06; A61B 6/405; A61B 6/52; A61B 6/5205; A61B 6/4441; A61B 6/488; G06T 11/006; G06T 11/005; G06T 11/008
  See application file for complete search history.

(56) References Cited

U.S. PATENT DOCUMENTS

| | | | |
|---|---|---|---|
| 5,204,627 A * | 4/1993 | Mistretta et al. | 324/309 |
| 6,768,782 B1 * | 7/2004 | Hsieh et al. | 378/8 |
| 6,983,182 B2 * | 1/2006 | Mistretta | 382/131 |
| 7,702,074 B2 * | 4/2010 | Sakaguchi et al. | 378/4 |
| 2006/0198499 A1 * | 9/2006 | Spies et al. | 378/207 |
| 2010/0067766 A1 * | 3/2010 | Vija | 382/131 |
| 2013/0279783 A1 * | 10/2013 | Schmitt et al. | 382/131 |

OTHER PUBLICATIONS

"Motion-Compensated and Gated Cone Beam Filtered Back-Projection for 3-D Rotational X-Ray Angiography" Schaefer et al., IEEE Trans Med Imaging. vol. 25, No. 7, pp. 898-906, (2006).
"Volume-of-interest (VOI) imaging in C-arm flat-detector CT for high image quality at reduced dose", Kolditz et al. Medical Physics; vol. 37; No. 6; pp. 2719-2730, (2010).

(Continued)

*Primary Examiner* — Glen Kao
(74) *Attorney, Agent, or Firm* — Schiff Hardin LLP (57) ABSTRACT

In a method and x-ray device to determine a three-dimensional target image data set showing at least one partial region of interest of an acquisition region, wherein the image data of the three-dimensional target image data set are reconstructed from two-dimensional projection images acquired from various projection directions, first projection images are acquired without a collimation of the radiation source from first projection directions and a three-dimensional overview image data set of the acquisition region is reconstructed from the first projection images. The partial region of interest is selected in the overview image data set. Second projection images are acquired, with collimation at the partial region, from second projection directions, the second projection directions differing from the first projection directions. The target image data set showing the acquisition region and the partial region of interest is reconstructed from all first and second projection images.

17 Claims, 4 Drawing Sheets

(56) References Cited

OTHER PUBLICATIONS

"3-D Reconstruction of dynamic high contrast objects for C-Arm CT-3-D", Rohkohl Diplomarbeit in Computer Science, Friedrich-Alexander Universtiy Erlangen, Nurnberg, Germany (2009).

"Cone.beam ROI Reconstruction using the Laplace Operator"; Dennerlein, 11th International Meeting on Fully Three-dimensional Image Reconstruction in Radiology and Nuclear Medicine, Jul. 11-15, Potsdam; pp. 80-83; (2011).

* cited by examiner

METHOD AND X-RAY DEVICE TO DETERMINE A THREE-DIMENSIONAL TARGET IMAGE DATA SET

BACKGROUND OF THE INVENTION

1. Field of the Invention

The present invention concerns a method to determine a three-dimensional target image data set showing at least one partial region of interest of an acquisition region, of the type wherein the image data of the three-dimensional target image data set are reconstructed from two-dimensional projection images acquired from various projection directions. The invention also concerns an x-ray device for implementing such a method.

2. Description of the Prior Art

Methods to reconstruct a three-dimensional image data set from two-dimensional projection images that were acquired from various projection directions are widely known. For example, it is possible to process the two-dimensional projection images in iterative methods or methods of filtered back-projection in order to determine a three-dimensional reconstruction image data set. Such procedures are mostly used in fields in which spatial information is also desired. In addition to computed tomography (CT), methods similar to computed tomography are known for x-ray devices with a C-arm and for tomosynthesis. The methods of computed tomography have also been used for some time in other x-ray systems (such as flat panel detector x-ray systems) in interventional and diagnostic environments to enable a high-quality volumetric imaging.

The achievable three-dimensional image quality within the acquisition region (field of view, FOV) depends on the reconstruction method that is used, but the image quality is principally theoretically limited by the selection of the acquisition parameters particularly the acquisition trajectory, the acquisition positions and the resolution of the x-ray detector that is used, thus the projection image count and the pixel size, as well as the x-ray dose that is used.

Consequently, in the prior art it is typical to select these acquisition parameters appropriately in the design of a measurement protocol in order to acquire sufficient 3D image information for a meaningful evaluation. For example, it is known to acquire approximately 400 projection images using a 2×2 binning for applications at C-arm x-ray devices with the goal of a good low contrast resolution. For tomosynthesis screening of a female breast, a very high pixel resolution (consequently no binning) is typically selected in the acquisition. The acquisitions deliver the desired high image quality across the entire acquisition region. A disadvantage of such methods similar to computed tomography is the high radiation exposure to which the patient is exposed because of the acquisition of the large number of projection images in the acquisition region.

It is often unnecessary to acquire the entire three-dimensional acquisition region (field of view) with the same image quality. Often, only partial regions of interest need to be evaluated more precisely, for example tumors in the tissue, cartilage between joint bones or fractures. These partial regions should be shown with as high a quality as possible, but a poorer quality would be sufficient for the surroundings. A problem, however, is that before beginning the acquisition, the precise position of these partial regions of interest in the image volume is frequently unknown.

In order to be able to examine a partial region of interest more precisely, methods have been proposed that address the aforementioned problem. If a three-dimensional image data set is calculated from an acquired sequence of projection images, and the three-dimensional image data set has approximately consistently high quality over the entire acquisition region, then if only a partial region thereof is of interest, a (digital) zoom function can be used in the visualization in order to show the partial region of interest enlarged. In this way details can be visually emphasized, but a gain in image information is not provided by a (digital) zoom.

In an article by D. Kolditz et al., "Volume-of-interest (VOI) imaging in C-arm flat-detector CT for high image quality at reduced dose", Med. Phys. 37 (6), June 2010, Pages 2719-2730, it is proposed to initially implement a low-dose scan from which a three-dimensional reconstruction image data set is reconstructed in which the partial region of interest is localized. A second scan subsequently takes place along the same scan path (acquisition trajectory) but with a higher x-ray dose and with collimation at the partial region of interest so that the radiation is focused only on the localized partial region of interest (often also designated as ROI). The final image result—thus the target image data set—is then reconstructed from the projection images of the second scan.

SUMMARY OF THE INVENTION

An object of the present invention is to provide a further increased image quality in selective partial regions of an acquisition region that have been identified as important, without exposing the examination subject to an overly high radiation dose.

This object by a method in accordance with the invention wherein first projection images are acquired without collimation of the radiation source that is used from first projection directions, and a three-dimensional overview image data set of the acquisition region is reconstructed from the first projection images.

The partial region of interest is selected in the overview image data set. Second projection images are acquired with collimation at the partial region from second projection directions that differ from the first projection directions.

The target image data set showing the acquisition region and the partial region of interest is reconstructed from all first and second projection images.

In the method according to the invention it is possible to improve the image quality in a partial region of interest in a target image data set that shows the entire acquisition region, in which method a type of incremental gain of image information is achieved within the partial region of interest selected in the respective current acquisition region. This gain is achieved by additional scans respectively collimated on only the partial region of interest (consequently the second projection images). The basic idea is to acquire the new second projection images from projection directions from which no projection image (thus no first projection image) has previously been acquired, for example from intermediate angle positions. In this way it is ensured that the second projection images will actually supply new information about the examination subject (specifically the partial region of interest).

All projection data, thus all first and second projection images, enter into the calculation of the respective current target image data set, which represents a marked difference from the aforementioned article by D. Kolditz. The method achieves, without an excessive radiation dose, a presentation in the image of the selected partial region of interest as desired in a very high quality (in particular in a high resolution and/or high contrast with low noise and fewer artifacts), in contrast to which the surroundings (which are less relevant to the evaluation) are shown in a lower image quality.

The method according to the invention can thus be considered as a form of magnifying glass that, in contrast to conventional magnifier or zoom functions, not only generates a digital enlargement/improvement of the image content in the partial region of interest but also delivers a higher image quality because new information (the second projection images) are acquired and taken into account in the calculation.

Relative to the prior art, the described method consequently has the following advantages. A very low total dose is radiated in the acquisition region in comparison to conventional methods, in which the image quality is created at an equally high level across the entire acquisition region. All acquired projection data contribute to the image in the reconstruction of the final image data set, meaning that no projection data are acquired from projection directions that have already been considered, so an acquisition of redundant data is avoided. Finally, the method according to the invention generates a target image data set at full size but with variable quality. Both a rough orientation and a very high image quality in selected partial regions are thus possible.

According to the invention, the selection of the partial region takes place automatically at least in part, such as on the basis of a segmentation of the overview image data set. It is thus possible to apply evaluation algorithms (in particular segmentation algorithms, possibly using additional information such as an anatomical atlas) to the overview image data set in order to determine the partial region of interest in a preferably completely automatic manner, for example on the basis of pre-established examination information. Also conceivable is a semiautomatic procedure in which different partial regions are segmented from the overview image data set and offered for selection to the user.

It is also conceivable for the selection of the partial region of interest to take place manually, for example by a user marking the target region of interest directly in a presentation of the overview image data set via an input unit (a mouse, for example).

In all of these cases, the first projection images consequently serve to construct an overview image data set that delivers the necessary orientation in order to enable the selection of the partial region of interest.

In a further embodiment of the present invention, in addition to the collimation, at least one additional acquisition parameter is adapted in the acquisition of the second projection images. It is thus conceivable to not only conduct a collimation at the partial region of interest as described, but also to adapt further acquisition parameters such that the information that is additionally acquired via the second projection images, has a high image quality. The adaptation of the additional acquisition parameter to an increase of the resolution and/or an increase of the contrast takes place.

Various adaptations of additional acquisition parameters are possible. The x-ray dose can be increased as such an additional acquisition parameter. For example, this can contribute to a contrast increase in the partial region of interest. It is also possible to reduce binning. If pixels of the x-ray detector are consequently merged in the preceding acquired projection images such as to accelerate the readout process and/or the evaluation, it is possible to reduce the binning (meaning to merge fewer pixels or to even discard them entirely) when the second projection images are acquired, such that a higher resolution is provided in the partial region of interest. As an additional example, an x-ray spectrum that is suitable for acquisition of the partial region is set. The x-ray spectrum is among the acquisition parameters that can be adapted, because different x-ray spectra can be particularly suited to soft tissue, bones, contrast agent and other target substances of interest.

Preferably, fewer than 100 (in particular 15-25) first projection images can be acquired. In this embodiment, only a very few first projection images that cover correspondingly few projection directions are consequently determined, such that overall a very low x-ray dose is applied as compared to a conventional procedure. It is intentionally accepted that the overview image data set that is reconstructed from these projections may exhibit artifacts and inaccuracies, but nevertheless such an overview image data set allows at least a rough localization of the partial region of interest to be made, automatically (at least in part) and/or by a user. In the extreme case it is possible to acquire only ten first projection images.

In a preferred embodiment of the present invention, projection directions situated at least in part between two first projection directions can be selected along the same acquisition trajectory as the second projection directions. For acquisition of the first and second projection images, it is thus possible to select the same acquisition trajectory such as a circular path (orbit), with the second projection images filling "gaps" between the acquisition positions of the first projection images. For example, an acquisition position for second projection images can always be in the middle between two acquisition positions of the first projection images, but it is also possible to fill the "gaps" with multiple second projection images from corresponding projection directions.

In a further embodiment of the method, to determine the target image data set a reconstruction image data set can be determined from the second projection images, with the target image data set being created by a pixel-by-pixel addition of the image data of the overview image data set and the reconstruction image data set. The pixels may be individually weighted. Such an additive superposition is particularly advantageous when the overview image data set and the reconstruction image data set have been determined on the basis of algorithms for filtered back-projection, which (as is generally known) process the projection data linearly. In this case, line artifacts that are still contained in the overview image data set and/or the reconstruction image data set are reduced via undersampling. An update of the overview image data set thus takes place as soon as new second projection images have been acquired. The selected partial region of interest is better presented in the target image data set than in the overview image data set, but also better than in the reconstruction image data set, since the entirety of the previously present projection image information enters into the calculation.

As noted, a weighting of the pixels can be implemented. Specifically, weightings that are pixel-dependent can be used to normalize the reconstruction. This means that weighting factors can be used that allow a normalization of the reconstruction for every image point pixel x. If the target image data set is generally (as described above) determined by a weighted addition, this can be expressed as:

$$f = a1(x)f1(x) + a2(x)f2(x).$$

wherein f designates the image data of the target image data set, f1 designates the image data of the overview image data set, and f2 designates the image data of the reconstruction image data set, and a1 and a2 are the weightings.

In an embodiment for a simple selection of the weighting factors, the weighting factors a(x) result for every image point x and both the overview image data set and the reconstruction image data set, as $$a(x)=(N1+N2)/(w1(x)+w2(x)),$$

wherein N1 designates the total number of the first projection images; N2 designates the total number of second projection images; w1(x) designates the number of first projection images in which the image point x is located in the radiation region exposed by x-rays; and w2(x) designates the number of second projection images in which the image point x is located in the radiation region exposed by x-rays. In this case, a1(x)=a2(x)=a(x) thus applies. An effective normalization is thereby achieved. Naturally, other definitions of the weighting are also possible.

In an alternative embodiment of the present invention, the target image data set is determined by a completely new reconstruction under consideration of the projection data of all first and second projection images. Instead of an addition of individually reconstructed three-dimensional image data sets, it is thus also possible to implement a complete reconstruction.

In a further embodiment of the present invention, a truncation correction is applied to the second projection images and/or a reconstruction image data set reconstructed from these. Because the second projection images generally exhibit a strong lateral truncation due to the selection of the smaller region of interest, a truncation correction is suggested for the reconstruction of the target image data set in general, in the reconstruction image data set in the first embodiment described above. The truncation correction can take place in an extrapolation of projection image data under consideration of the overview image data set. Because the overview image data set shows the entire acquisition region, it is thus possible to extrapolate the projection image data of the second projection images so that they correspond to the image data of the overview image data set in order to enable a good truncation correction. Less preferably, it is also possible to conduct a model-based data extrapolation or to use another truncation correction method to reduce truncation artifacts, for example a correction method proposed by the article by F. Dennerlein, "Cone-beam ROI reconstruction using the Laplace operator", Proc. Fully 3D 2011, Pages 80-83, 2011.

In a further embodiment of the present invention, a new partial region of interest (that is included in the previous partial region of interest) is selected in the image data set as a new overview image data set, whereupon a new target image data set is reconstructed after acquisition of new second projection images under collimation at the new partial region of interest. This means that the procedure according to the invention is usable repeatedly for different partial region of interests, so as to achieve an increasingly progressing refinement, such that the image quality in successively defined partial regions can always be further improved (which corresponds to a type of incremental magnifying glass), wherein additional supplemental information are always acquired for the presently selected region of interest from projection directions that have not previously been scanned. The image quality can be improved up to the desired degree. It is advantageous for the new partial region of interest to be completely contained in the previous partial region of interest. The method according to the invention can consequently be repeated until the desired image quality is achieved within the region of interest, such as for a feature within the acquisition region that is relevant to the evaluation. If increasingly smaller partial regions of interest are selected, with each new scan of second projection images the collimation is increased so that the additional dose that is employed successively decreases.

Because multiple acquisition processes (at least two acquisition processes) are required, it is preferable for movements of the examination subject (such as the patient, but at least of the acquisition region) to be avoided. For example, this can be achieved by an appropriate fixing of the patient or of the acquisition region.

However, it is also possible to implement a movement correction by processing within the scope of the present invention. For example, to correct a movement, the overview image data set is registered with the reconstruction image data set which was determined from the second projection images. Registration information can be determined that enables the compensation of patient movements between the scan passes. It is additionally possible to bring about a registration in the projection image space, which can then already be taken into account in the reconstruction of image data sets (in particular within the scope of a back-projection). For this purpose, one or more fewer projection images of the first and second projection images can be acquired from the same projection directions, which means that at least one pair of first and second projection images is acquired from the same projection direction, with registration information being determined by comparison of first and second position images of the same projection direction.

In addition to the method, the present invention also concerns an x-ray device having a control device designed to implement the method according to the invention. Such an x-ray device can be a C-arm x-ray device, for example, with which computed tomography-like projection images can be acquired from different projection angles and three-dimensional image data sets can be reconstructed. The x-ray device can be a tomosynthesis x-ray device with which the breast and the lung can be examined, for example. All embodiments with regard to the method according to the invention apply analogously to the x-ray device according to the invention, with which the same advantages can consequently be achieved.

Such a control device—consequently the x-ray device—can include a reconstruction unit that is designed for reconstruction of the target image data set. A display device can be used in order to display image data sets, and an input device can also be provided, particularly when an at least partial manual selection of the partial region of interest takes place. A collimation device (that can have, for example, one or more diaphragms) is provided at the radiation source. The collimation device is thereby automatically adjustable, controlled by the control device. The acquisition operation is also generally controlled by the control device, in particular the operation of the radiation source and the x-ray detector as well as the movement of the acquisition arrangement comprising radiation source and x-ray detector or of the radiation source along the acquisition trajectory.

The method according to the invention can be used in a multitude of fields of application. In particular, the described method is suitable for a number of acquisition geometries, in particular for circular acquisition trajectories with angle ranges of approximately 200°-360° in C-arm computed tomography, for tomosynthesis-like acquisition geometries (for example in mammography), in bone imaging or for the screening of lung cancer, and for special, compact cone beam geometries, for example as are used in breast computed tomography or in dedicated extremity scanners.

DESCRIPTION OF THE PREFERRED EMBODIMENTS

Figure 1:
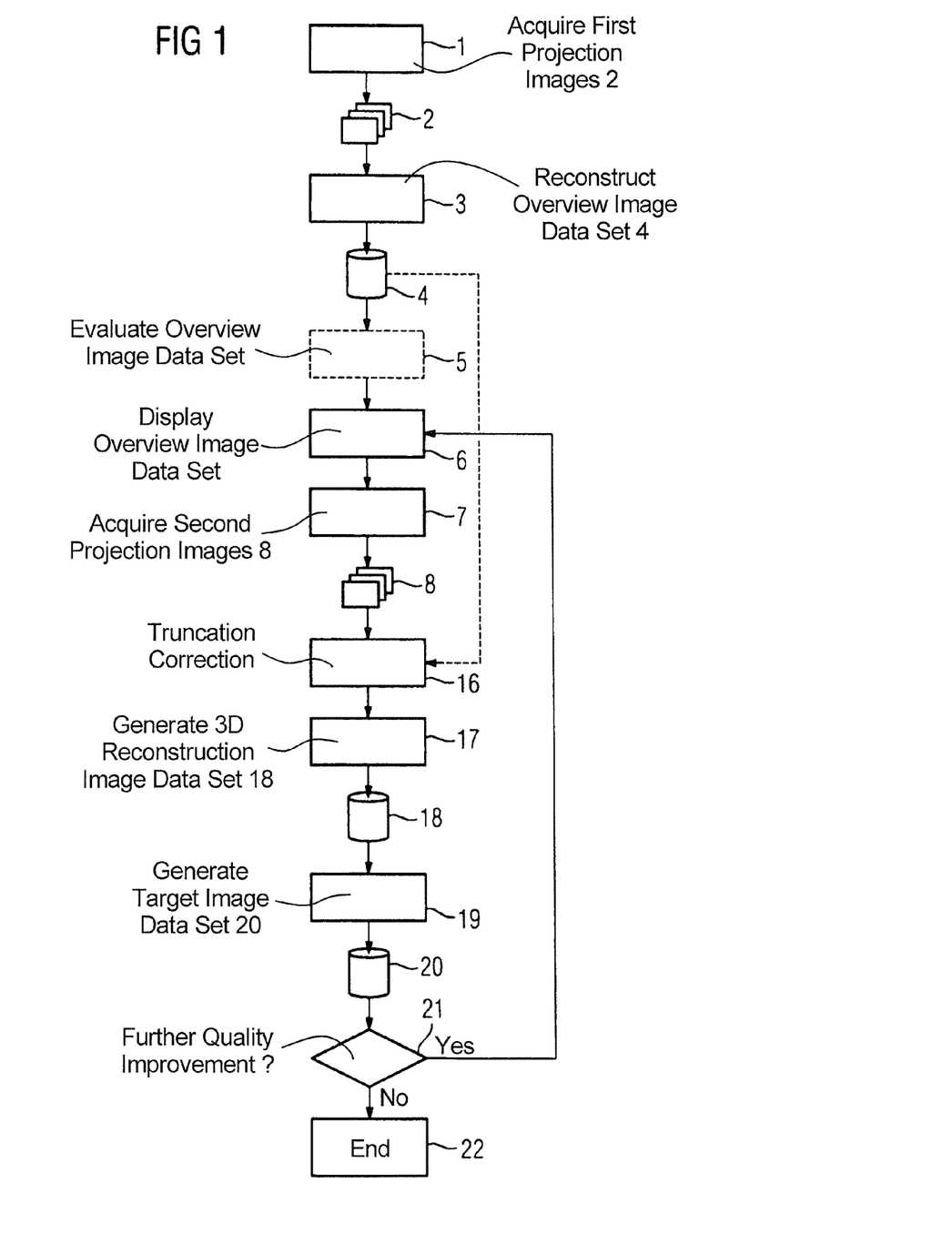
FIG. 1 is a flowchart of an embodiment the method according to the invention.

FIG. 1 is a flowchart of an exemplary embodiment of the method according to the invention. In Step 1, first projection images 2 are acquired along an acquisition trajectory, wherein this is performed without a collimation of the radiation source that is used. Along the acquisition trajectory, defined acquisition positions are used that correspond to first projection directions of the first projection images.

In Step 3, an overview image data set 4 that shows the entire acquisition region (because no collimation whatsoever has been conducted) is reconstructed from the first projection images 2 using a filtered back-projection algorithm.

In Step 5, this overview image data set is now optionally evaluated in order to automatically segment possible partial regions of interest. In this exemplary embodiment, a presentation of the overview image data set 4 is then displayed in a Step 6 so that a user can select a partial region of interest in which he desires higher-quality image data in a three-dimensional reconstruction. It is thereby noted that the selection of a partial region of interest in Step 6 can also occur wholly automatically.

Although only twenty first projection images were acquired in the present exemplary embodiment—wherein a low x-ray dose was additionally applied—the overview image data set 4 is sufficient in order to determine the position of the partial region of interest (which can correspond to a tumor, a cartilage or the like) with sufficient precision.

Because this first partial region of interest was selected in Step 6, in Step 7 second projection images 8 are acquired. This occurs on the one hand such that a collimation at the partial region of interest has been conducted, but on the other hand from second projection directions that differ from the first projection directions, as this should be presented in detail via the principle drawing in FIG. 2.

Figure 2:
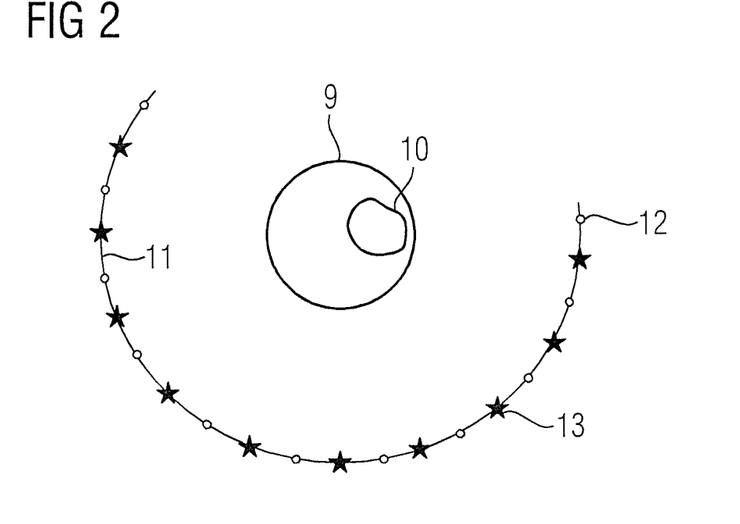
FIG. 2 is a first illustration for the selection of acquisition positions along an acquisition trajectory.

There the maximum possible acquisition region 9 (field of view, FOV) is initially shown that is depicted in the overview image data set 4 whose first projection images 2 were acquired without collimation. The region of interest 10 lies within the acquisition region 9. An orbit around the subject to be acquired (consequently the acquisition region 9) is hereby selected as an acquisition trajectory 11 for the first and second projection images 2, 8. The circles and stars thereby show acquisition positions 12, 13 along the acquisition trajectory 11 that consequently correspond to different projection directions. The acquisition positions 12 (circles) thereby correspond to acquisition positions of the first projection images 2; the acquisition positions 13 (stars) that lie between acquisition positions 12 are acquisition positions for the second projection images 8. Ultimately, scanning "gaps" are filled by the second projection images 8 for at least the region 10 of interest.

Figure 3:
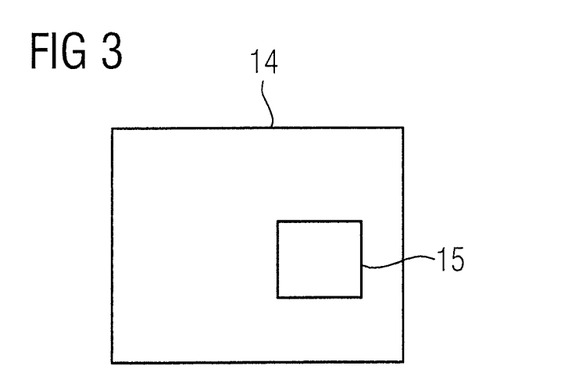
FIG. 3 is a schematic illustration of the collimation given the selection according to FIG. 2.

FIG. 3 schematically shows the conducted collimation. The beam field striking the x-ray detector (indicated by the box 14) thereby corresponds to the situation without a collimation, thus for the first projection images 2, while the box 15 represents the beam field striking the x-ray detector for the collimation on the region 10 of interest for the second projection images 8.

It is noted that, in the acquisition of the second projection images 8 in Step 7, additional acquisition parameters can also be adapted in order to increase the quality of the image data—for example, an x-ray dose can be increased, a binning can be reduced and/or a suitable x-ray spectrum can be selected.

In Step 16, a truncation correction of the second projection images 8 is then conducted after this has been laterally truncated. Data of the second projection images 8 are thereby extrapolated, wherein the overview image data set 4 is taken into account, which means that the extrapolation takes place such that the supplemented projection image data correspond to the image data included in the overview image data set 4.

After the truncation correction, in Step 17 a three-dimensional reconstruction image data set 18 is determined using a filtered back-projection algorithm.

In Step 19, the overview image data set 4 is then updated to a target image data set 20 using the reconstruction image data set 18, wherein a weighted per-image point addition of the overview image data set 4 and the reconstruction image data set 18 takes place. For the weightings serving for the normalization, the weighting a(x) (defined above) is used for both image data sets 4, 18.

Alternatively, it is also possible to conduct a completely new reconstruction on the basis of the first projection images 2 and the second projection images 8. However, in all exemplary embodiments of the method according to the invention it is essential that all first and second projection images 2, 8 are taken into account in order to determine the target image data set 20.

The target image data set 20 now includes the entire acquisition region 9, and the region of interest 10 at higher quality. It can now be displayed to a user. This user can now decide (Step 21) whether he desires a further quality improvement in a further partial region of interest. If this is the case, the target image data set 20 is used as a new overview image data set and a selection of a new partial region of interest takes place, for which Steps 6-19 are implemented again in order to obtain an additional, updated, improved target image data set 20. If the quality satisfies the user, the method is ended in Step 22.

Figure 4:
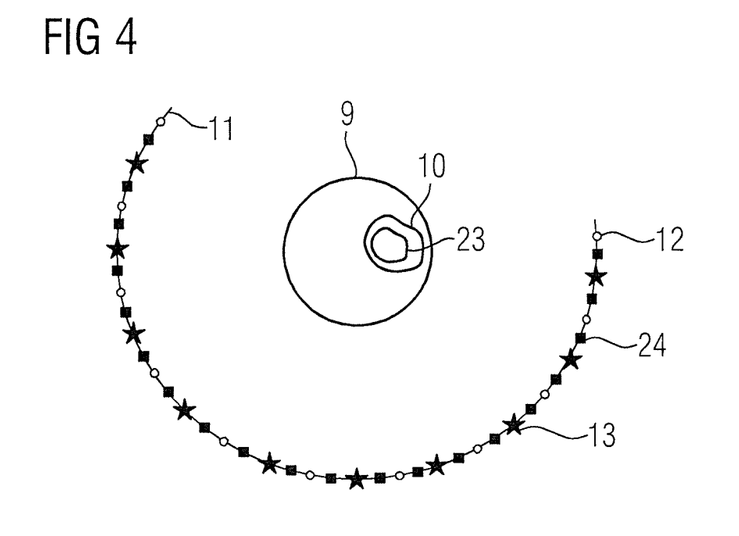
FIG. 4 is a second illustration for the selection of acquisition positions along the acquisition trajectory.
Figure 5:
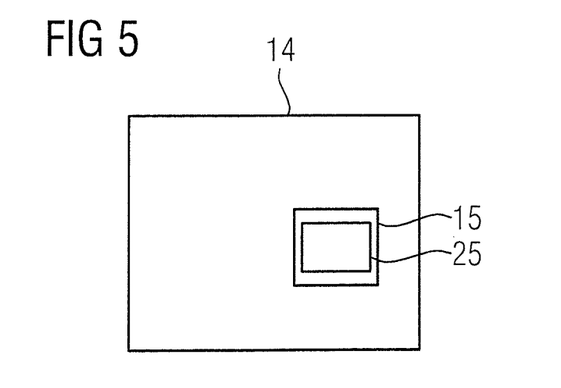
FIG. 5 is an illustration of the collimation given a selection according to FIG. 4.

Given the selection of a second, new partial region of interest 23 (that advantageously lies within the previous partial region of interest 10), the situation is explained in FIGS. 4 and 5. The acquisition trajectory 11 is used again for all acquisitions of projection images 2, 8. The acquisition positions 12 (circles) for the first projection images and the acquisition positions 13 (stars) for the first selected region of interest 10 are again apparent. The acquisition positions 24 for the second, newly selected region of interest 23 has presently been selected so that they lie respectively between one of the acquisition positions 12 and one of the acquisition positions 13. Naturally, other possibilities are also conceivable in which fewer second projection images 8 collimated at the region of interest 23 are acquired.

Analogous to FIG. 3, FIG. 5 shows the conducted collimation using boxes 14, 15 and 25 indicating beam fields at the x-ray detector. The box 25 symbolizes the collimation for the region of interest 23 that lies within the previous region 10 of interest. The box 25 consequently lies within the box 15.

Figure 6:
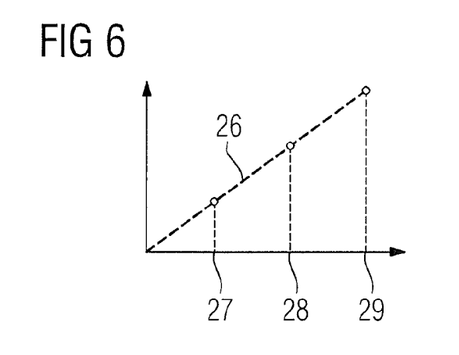
FIG. 6 is a graph to explain the increase of the image quality.

If—as shown—the further partial regions of interest 23 are always selected within the previous partial regions of interest 10, in spite of the information gain for the actual relevant feature the radiation exposure of the patient only insignificantly increases. This is shown by the graphs in FIGS. 6 and 7. There the image quality in the last selected partial region of interest 23 is plotted against the projection image set, and in fact under the assumption that each acquisition of second projection images 8 delivers the same number of second projection images 8 as the original acquisition of first projection images 2 for the entire acquisition region. A linear correlation then exists, as is shown by the indicated straight line 26. The position 27 relates to the acquisition of first projection images 2 in Step 1; at the position 28 the second projection images 8 for the first selected partial region of interest 10 are added; finally, at the position 29 the second projection images 8 for the second selected partial region of interest 23 are added.

Figure 7:
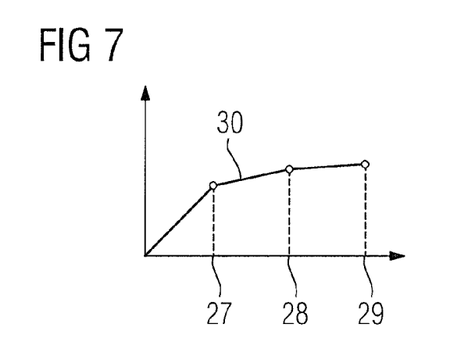
FIG. 7 is a graph to explain the increase of the dose in the acquisition region.

In FIG. 7, the total dose over the acquisition region is plotted against the projection image set, wherein the positions 27, 28 and 29 are shown in turn. Due to the collimation, the radiation exposure in the acquisition region only rises extremely slowly, as the curve 30 shows.

Figure 8:
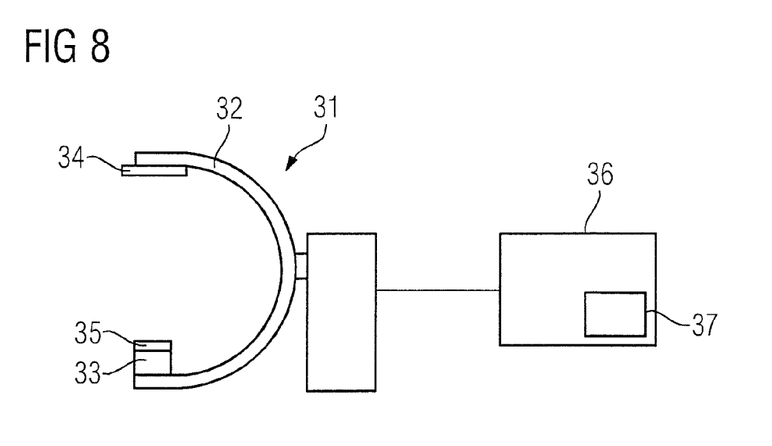
FIG. 8 shows an x-ray device according to the invention.

Finally, FIG. 8 shows a principle drawing of an x-ray device 31 according to the invention. A C-arm x-ray device 21 has a C-arm 32 at which are arranged opposite one another a radiation source 33 and an x-ray detector 34 fashioned as a flat panel detector. Various acquisition trajectories—in particular orbits—can be realized via degrees of freedom of movement of the C-arm 32. At the radiation source 33, a collimation device 35 is provided via which the collimation of the cone beam (which collimation is described with regard to FIGS. 3 and 5) can be achieved.

The operation of the x-ray device 31 is controlled via a control device 36 that is designed to implement the method according to the invention. This means that the acquisition arrangement at the C-arm 32 can be accordingly controlled just like the collimation device 25 in order to realize the acquisition of the projection images 2, 8 along the acquisition trajectory 11 and the corresponding collimation, as well as to realize possibly provided further adaptation of the acquisition parameters. A reconstruction unit 37 is additionally provided in the control device 36, in which reconstruction unit 37 the corresponding reconstructions and possibly the described corrections can be conducted.

In the exemplary embodiment described herein, it has been assumed that the subject to be acquired (in particular a patient) has remained immobile. As described above, movement correction algorithms can also be realized for the case of patient movements in the acquisition region, in particular via registration.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to determine a three-dimensional target image data set showing at least one partial region of interest of an acquisition region, comprising:
    operating an x-ray image acquisition system, comprising a radiation source, to acquire first projection images without collimation of said radiation source, from first projection directions;
    in a processor, reconstructing a three-dimensional overview image data set of the acquisition region from said first projection images;
    selecting the partial region of interest in the overview image data set;
    operating said x-ray image acquisition system to acquire second projection images with collimation of said partial region, from second projection directions that all differ from said first projection directions, with none of said second projection directions being the same as any of said first projection directions; and
    in said processor, reconstructing said target image data set showing said acquisition region and said partial region of interest, from all of said first and second projection images, and making said target image data set available in electronic form at an output of the processor, as a data file.

2. A method as claimed in claim 1 comprising selecting said partial region at least partially automatically in said processor.

3. A method as claimed in claim 2 comprising selecting said partial region in said processor by executing a segmentation algorithm on said overview image data set.

4. A method as claimed in claim 1 comprising adapting at least one acquisition parameter of said x-ray image acquisition system, in addition to collimation of the radiation, to acquire said second projection images.

5. A method as claimed in claim 4 comprising adapting said acquisition parameter to increase at least one of resolution and contrast of said second projection images.

6. A method as claimed in claim 4 comprising adapting, as said acquisition parameter, by at least one of increasing an x-ray dose of said radiation, reducing binning, and setting an x-ray spectrum, to improve acquisition of said partial region.

7. A method as claimed in claim 1 comprising acquiring fewer than 100 first projection images.

8. A method as claimed in claim 1 comprising acquiring a number of first projection images in a range between 15 and 25 first projection images.

9. A method as claimed in claim 1 comprising selecting, as said second projection directions, projection directions that are located between two of said first projection directions, along a same acquisition trajectory.

10. A method as claimed in claim 1 comprising reconstructing said target image data set by reconstructing a reconstruction image data set from said second projection images and reconstructing said target image data set with a weighted, pixel-by-pixel addition of image data in said overview image data set and image data in said reconstruction image data set.

11. A method as claimed in claim 10 comprising selecting weightings of said pixels to normalize the reconstruction of said target image data set.

12. A method as claimed in claim 10 comprising selecting weighting factors $a(x)$ for each pixel x in both the overview image data set and the reconstruction image data set as $a(x)=(N1+N2)/(w1(x)+w2(x))$, wherein N1 designates a total number of the first projection images, N2 designates a total number of second projection images, $w1(x)$ designates a number of first projection images in which the image point x is located in the radiation region exposed by x-rays, and $w2(x)$ designates a number of second projection images in which the image point x is located in the radiation region exposed by x-rays.

13. A method as claimed in claim 1 comprising reconstructing said target image data set as a new reconstruction using projection data of all of said first and second projection images.

14. A method as claimed in claim 1 comprising, in said processor, applying a truncation correction to said second projection images.

15. A method as claimed in claim 14 comprising executing said truncation correction by extrapolating said second projection image data dependent on said overview image data set.

16. A method as claimed in claim 1 comprising selecting a new partial region of interest in said target image data set and using said new partial region of interest as a new overview image data set, and acquiring new second projection images, and reconstructing a new target image data set from said new second projection images and said new partial region of interest.

17. An x-ray system comprising:

an x-ray image acquisition device comprising a radiation source;

a control unit configured to operate said x-ray image acquisition device to acquire first projection images without collimation of said radiation source, from first projection directions;

a processor configured to reconstruct a three-dimensional overview image data set of an acquisition region from said first projection images;

said processor being configured to receive or make a selection of a partial region of interest in the overview image data set;

said control unit being configured to operate said x-ray image acquisition device to acquire second projection images with collimation of said partial region, from second projection directions that all differ from said first projection directions, with none of said second projection directions being the same as any of said first projection directions; and said processor being configured to reconstruct a target image data set showing said acquisition region and said partial region of interest, from all of said first and second projection images, and to make said target image data set available in electronic form at an output of the processor, as a data file.

* * * * *